(12) United States Patent
Perry

(10) Patent No.: US 9,849,108 B2
(45) Date of Patent: Dec. 26, 2017

(54) COMPOSITION WITH PHARMACOLOGICAL EFFECT FOR VAPORIZING AND METHOD

(71) Applicant: Stephen C. Perry, Norwood, MA (US)

(72) Inventor: Stephen C. Perry, Norwood, MA (US)

( * ) Notice: Subject to any disclaimer, the term of this patent is extended or adjusted under 35 U.S.C. 154(b) by 0 days.

(21) Appl. No.: 15/144,039

(22) Filed: May 2, 2016

(65) Prior Publication Data

US 2016/0256435 A1    Sep. 8, 2016

Related U.S. Application Data

(62) Division of application No. 13/973,509, filed on Aug. 22, 2013, now Pat. No. 9,326,967.

(51) Int. Cl.

| | | |
|---|---|---|
| *A61K 31/352* | (2006.01) | |
| *A61K 36/185* | (2006.01) | |
| *A61K 36/28* | (2006.01) | |
| *A61K 47/14* | (2017.01) | |
| *A61K 9/00* | (2006.01) | |
| *A61M 11/04* | (2006.01) | |
| *A61L 9/14* | (2006.01) | |

(52) U.S. Cl.
CPC ............ *A61K 31/352* (2013.01); *A61K 9/007* (2013.01); *A61K 36/185* (2013.01); *A61K 36/28* (2013.01); *A61K 47/14* (2013.01); *A61K 9/0073* (2013.01); *A61L 9/14* (2013.01); *A61M 11/04* (2013.01)

(58) Field of Classification Search
CPC ... A61K 31/352; A61K 9/0073; A61M 11/04; A61L 9/14
See application file for complete search history.

*Primary Examiner* — Savitha Rao
(74) *Attorney, Agent, or Firm* — Johnson & Martin, P.A.; James David Johnson

(57) ABSTRACT

A composition is provided that includes a cannabinoid capable of inducing a pharmacological effect, an ester, a condensation aerosol, and a carrier liquid solution of food grade materials. The cannabinoid may include a bio-active ingredient receivable by a cannabinoid receptor and/or an acetylcholine receptor. The pharmacological effect may be produced by reception of tetrahydrocannabinol, cannabidiol, or mixtures thereof. The composition may also include ethanol, flavoring agents, and aromatherapy agents. The composition is deliverable to a user via vaporization. A method is provided for creating a pharmacological effect using the composition.

16 Claims, No Drawings

COMPOSITION WITH PHARMACOLOGICAL EFFECT FOR VAPORIZING AND METHOD

CROSS REFERENCE TO RELATED APPLICATIONS

This application is a divisional application of and claims priority from U.S. patent application Ser. No. 13/973,509 filed on Aug. 22, 2013. The foregoing application is incorporated in its entirety herein by reference.

FIELD OF THE INVENTION

The invention relates to a composition with a pharmacological effect. More specifically, the invention relates to a composition with a pharmacological effect that can be administered via vaporization.

BACKGROUND

Combusting and inhaling an organic compound can cause a user to take undesired chemicals and substances into his or her body. To overcome some of these undesirable consequences of smoking, devices for vaporizing compounds have been developed. For example, electronic cigarettes are commonly used to inhale vaporized nicotine solutions. However, there lacks a composition and delivery mechanism for medicinal and recreational compounds based on cannabinoids.

Traditional combustion- and smoking-based cannabis intake practices undesirably enhance inhalation of noxious smoke compounds that pose respiratory hazards. More specifically, inhalation of combusted cannabis compounds may also include carcinogenic polynuclear (or "polycyclic") aromatic hydrocarbons (PAHs). These undesirable compounds are known byproducts of combustion that are commonly associated with smoking-related cancers. Additionally, inhalation of these combustion byproducts may lead to higher risk of bronchitis and respiratory infections.

Many states have decriminalized consumption of *cannabis* for treatment of medical conditions. Some states have decriminalized or legalized consumption of *cannabis* for recreational use. As a result, usage of cannabinoids and other *cannabis* derived substances may increase. However, not all potential users may wish to inhale combusted organic material to receive the pharmacological effect. Therefore, there exists a need for a composition for delivery of a cannabinoid that does not require inhalation of combusted organic material.

SUMMARY

The present invention provides a composition for delivery of a cannabinoid without requiring inhalation of a combusted organic material. The present invention provides an improved method for receiving a cannabinoid to produce a pharmacological effect. By receiving a bio-active ingredient of a composition including a cannabinoid, a user may benefit from medicinal and therapeutic treatment of a myriad of diseases, conditions, and symptoms presently addressed only by smoking *cannabis*. Benefits include pain relief, weight gain for cancer patients, weight gain for anorexic sufferers, and especially useful in treatment of diseases and conditions in the lungs and respiratory system.

The composition of the present invention may include a cannabinoid capable of inducing a pharmacological effect, an ester, a condensation aerosol, and a carrier liquid solution of food grade materials. The cannabinoid may include a bio-active ingredient receivable by a cannabinoid receptor and/or an acetylcholine receptor. The pharmacological effect may be produced by reception of tetrahydrocannabinol, cannabidiol, other cannabinoids, or mixtures thereof. The composition may also include ethanol, flavoring agents, and aromatherapy agents. The composition is deliverable to a user via vaporization. A method is provided for creating a pharmacological effect using the composition.

In another aspect, inhalation of a vaporized form of the composition provided by the present invention may assist with smoking cessation. In an embodiment of the present invention, the product may contain a tobacco essence, nicotine free tobacco essence, and/or flavoring to ease the transition away from tobacco products.

According to an embodiment of the present invention, a composition is provided including a cannabinoid, an ester, a condensation aerosol, and a carrier. The cannabinoid may be capable of inducing a pharmacological effect. The cannabinoid may be an endocannabinoid, a phytocannabinoid, or a synthetic cannabinoid. The carrier liquid solution may use food grade materials. The composition is absorbable by a mucosa via vaporization. The mucosa may include an oral mucous membrane. The carrier liquid solution may enhance sublingual delivery into the oral mucous membrane to provide accelerated onset of the pharmacological effect. The cannabinoid includes a bio-active ingredient receivable by a cannabinoid receptor or an acetylcholine receptor.

In another aspect, the cannabinoid may be derived from at least one cannabinoid source including *Cannabis sativa, Cannabis indica, Cannabis ruderalis, Echinacea purpurea, Echinacea angustifolia, Echinacea pallida, Acmella oleraca, Helichrysum umbraculigerum,* and *Radula marginata.*

In another aspect, the ester may be derived from the cannabinoid source.

In another aspect, the bio-active ingredient may include tetrahydrocannabinol, cannabidiol, cannabinol, dodeca-2E, 4E,8Z,10E/Z-tetraenoic-acid-isobutylamides, cannabigerol, cannabichromene, cannabicyclol, cannabivarin, tetrahydrocannabivarin, cannabidivarin, cannabichromevarin, cannabigerovarin, and cannabigerol monomethyl ether.

In another aspect, the pharmacological effect may be produced by reception of tetrahydrocannabinol, cannabidiol, or a mixture of the tetrahydrocannabinol and the cannabidiol by the cannabinoid receptor.

In another aspect, the composition may include ethanol.

In another aspect, the composition may include an absorption enhancing agent that creates a condition of polymorphism to enhance absorption into the mucosa.

In another aspect, the absorption enhancing agent may include at least one ingredient of dimethyl sulfoxide, plant lecithins, liposomes, food derived surfactants, and fatty alcohols.

In another aspect, the composition may include a flavoring agent.

In another aspect, the composition may include an aromatherapy agent.

According to an embodiment of the present invention, a composition is described for inducing a pharmacological effect. The composition may include a cannabinoid, an ester, a condensation, a carrier liquid solution, and an absorption enhancing agent. The cannabinoid may include a bio-active ingredient of tetrahydrocannabinol, cannabidiol, or a mixture of the tetrahydrocannabinol and the cannabidiol. The cannabinoid may be capable of inducing the pharmacological effect. The absorption enhancing agent may enhance absorption of the cannabinoid into mucosa by creating a condition of polymorphism. The bio-active ingredient is receivable by a cannabinoid receptor or an acetylcholine receptor. The composition is absorbable into the mucosa via vaporization.

In another aspect, the cannabinoid may be derived from at least one cannabinoid source selected from the list including *Cannabis sativa, Cannabis indica, Cannabis ruderalis, Echinacea purpurea, Echinacea angustifolia, Echinacea pallida, Acmella oleraca, Helichrysum umbraculigerum,* and *Radula marginata*.

In another aspect, the cannabinoid may include at least one a bio-active composition to activate a cannabinoid receptor including an endocannabinoid, a phytocannabinoid, and a synthetic cannabinoid.

In another aspect, the bio-active ingredient may include tetrahydrocannabinol, cannabidiol, cannabinol, dodeca-2E, 4E,8Z,10E/Z-tetraenoic-acid-isobutylamides, cannabigerol, cannabichromene, cannabicyclol, cannabivarin, tetrahydrocannabivarin, cannabidivarin, cannabichromevarin, cannabigerovarin, and cannabigerol monomethyl ether.

In another aspect, the mucosa may include an oral mucous membrane. The carrier liquid solution may enhance sublingual delivery into the oral mucous membrane to provide accelerated onset of the pharmacological effect.

In another aspect, the composition may include ethanol.

In another aspect, the condensation may be an aerosol. The absorption enhancing agent may include at least one ingredient of dimethyl sulfoxide, plant lecithins, liposomes, food derived surfactants, and fatty alcohols.

In another aspect, the composition may include a flavoring agent.

In another aspect, the composition may include an aromatherapy agent.

According to an embodiment of the present invention, a method aspect may be provided for creating a pharmacological effect using a composition. The method may include vaporizing the composition. The composition to be vaporized may include a cannabinoid capable of inducing the pharmacological effect, wherein the cannabinoid is an endocannabinoid, a phytocannabinoid, or a synthetic cannabinoid; an ester; a condensation aerosol; and a carrier liquid solution of food grade materials. The method may also include absorbing the composition into a mucosa. Additionally, the method may include receiving a bio-active ingredient of the composition by a cannabinoid receptor and/or an acetylcholine receptor.

In another aspect of the method, the mucosa may include an oral mucous membrane. The carrier liquid solution may enhance sublingual delivery into the oral mucous membrane to provide accelerated onset of the pharmacological effect.

In another aspect of the method, the cannabinoid may be derived from at least one cannabinoid source including *Cannabis sativa, Cannabis indica, Cannabis ruderalis, Echinacea purpurea, Echinacea angustifolia, Echinacea pallida, Acmella oleraca, Helichrysum umbraculigerum,* and *Radula marginata*.

In another aspect of the method, the ester may be derived from the cannabinoid source.

In another aspect of the method, the bio-active ingredient may include tetrahydrocannabinol, cannabidiol, cannabinol, dodeca-2E,4E,8Z,10E/Z-tetraenoic-acid-isobutylamides, cannabigerol, cannabichromene, cannabicyclol, cannabivarin, tetrahydrocannabivarin, cannabidivarin, cannabichromevarin, cannabigerovarin, and cannabigerol monomethyl ether.

In another aspect of the method, the pharmacological effect may be produced by reception of tetrahydrocannabinol, cannabidiol, or a mixture of the tetrahydrocannabinol and the cannabidiol by the cannabinoid receptor.

In another aspect of the method, the composition may include ethanol.

In another aspect of the method the composition may include an absorption enhancing agent that creates a condition of polymorphism to enhance absorption into the mucosa.

In another aspect of the method, the absorption enhancing agent may include at least one ingredient of dimethyl sulfoxide, plant lecithins, liposomes, food derived surfactants, and fatty alcohols.

In another aspect of the method, the composition may include a flavoring agent.

In another aspect of the method, the composition may include an aromatherapy agent.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control.

DETAILED DESCRIPTION

The present invention is best understood by reference to the detailed drawings and description set forth herein. Embodiments of the invention are discussed below with reference to the drawings; however, those skilled in the art will readily appreciate that the detailed description given herein with respect to these figures is for explanatory purposes as the invention extends beyond these limited embodiments. For example, in light of the teachings of the present invention, those skilled in the art will recognize a multiplicity of alternate and suitable approaches, depending upon the needs of the particular application, to implement the functionality of any given detail described herein beyond the particular implementation choices in the following embodiments described and shown. That is, numerous modifications and variations of the invention may exist that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

The present invention should not be limited to the particular methodology, compounds, materials, manufacturing techniques, uses, and applications, described herein, as these may vary. The terminology used herein is used for the purpose of describing particular embodiments only, and is not intended to limit the scope of the present invention. As used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" may be a reference to one or more steps or means and may include sub-steps and subservient means.

All conjunctions used herein are to be understood in the most inclusive sense possible. Thus, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. Structures described herein are to be understood also to refer to functional equivalents of such structures. Language that may be construed to express approximation should be so understood unless the context clearly dictates otherwise.

Unless otherwise defined, all terms (including technical and scientific terms) are to be given their ordinary and customary meaning to a person of ordinary skill in the art, and are not to be limited to a special or customized meaning unless expressly so defined herein.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," "desirable," or "exemplary" and words of similar meaning should not be understood as implying that certain features are critical, essential, or even important to the structure or function of the invention, but instead as merely intended to highlight alternative or additional features that may or may not be utilized in a particular embodiment of the invention.

Those skilled in the art will also understand that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations; however, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C" is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.).

All numbers expressing dimensions, quantities of ingredients, reaction conditions, and so forth used in the specification are to be understood as being modified in all instances by the term "about" unless expressly stated otherwise. Accordingly, unless indicated to the contrary, the numerical parameters set forth herein are approximations that may vary depending upon the desired properties sought to be obtained.

The invention provides a composition capable of being vaporized and received by a user. The invention includes a composition usable by existing vaporizers, such as electronic cigarettes. The composition may include at least a cannabinoid, an ester, a condensation, and a carrier liquid solution. After the composition has been vaporized, it may be received by a user to induce a pharmacological effect. A method is also provided for inducing a pharmacological effect using the composition.

The composition will now be discussed in greater detail. The composition may include a cannabinoid capable of inducing a pharmacological effect, an ester, a condensation, and a carrier liquid that may be formed using food grade materials. The composition may be absorbed by mucosa, for example, as a vapor and/or an aerosol. In one example, the mucosa may include an oral mucous membrane, which may receive the cannabinoid and carrier by enhanced sublingual delivery into the mucous membrane to provide an accelerated onset of the pharmacological effect. The cannabinoid may include a bio-active ingredient, which can be received by a cannabinoid receptor and/or acetylcholine receptor.

The cannabinoid will now be discussed in greater detail. A cannabinoid is a class of chemical compositions that activate cannabinoid receptors, which may affect the behavior of neurotransmitters in the brain. Cannabinoid receptors are defined herein to include CB1, CB2, and the acetylcholine receptor AChR. The cannabinoids may be used in any available form including, but not limited to keif, hashish, hash oil, and/or resin.

The cannabinoid may be an endocannabinoid, phytocannabinoid, and/or synthetically derived cannabinoid. Endocannabinoids may be produced naturally in the body by humans and animals. Phytocannabinoids may be found in *cannabis* and some other plants. Synthetic cannabinoids may be produced chemically by humans. For example, a phytocannabinoid may be extracted from a plant including, but not limited to, *Cannabis sativa, Cannabis indica, Cannabis ruderalis, Echinacea purpurea, Echinacea angustifolia, Echinacea pallida, Acmella oleraca, Helichrysum umbraculigerum*, and *Radula marginata*. Alternatively, the cannabinoid may at least partially include an endocannabinoid produced by an animal and/or a synthetically derived cannabinoid, without limitation.

Synthetic cannabinoids may encompass a variety of distinct chemical classes. These classes may include classical cannabinoids structurally related to THC. The synthetic cannabinoids may also encompass nonclassical cannabinoids, such as cannabimimetics, including the aminoalkylindoles, 1,5-diarylpyrazoles, quinolines, and arylsulphonamides as well as eicosanoids related to the endocannabinoids.

The most notable cannabinoid is the phytocannabinoid Δ9-tetrahydrocannabinol (THC), the primary psychoactive compound of *cannabis*. However, numerous other cannabinoids may be included in the composition with varied effects, including Δ8-tetrahydrocannabinol (THC), cannabidiol (CBD), cannabinol (CBN), and dodeca-2E,4E,8Z, 10E/Z-tetraenoic-acid-isobutylamides are the most prevalent natural cannabinoids. Other common cannabinoids that may be used in the composition include, but are not limited to, cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM). The dodeca-2E,4E,8Z,10E/Z-tetraenoic-acid-isobutylamides and other cannabinoids may be derived from species in the *echinacea* genus.

The ester will now be discussed in greater detail. The composition of the present invention may include food grade esters, such as fatty acid esters (FAEs). As will be appreciated by those of skill in the art, a FAE is a type of ester resulting from the combination of a fatty acid and an alcohol. The alcohol may be glycerol, for example, which may combine with the FAEs to produce monoglycerides, diglycerides, or triglycerides, all of which are components of vegetable fats and oils. Additional esters that may be used optimally include, but should not be limited to, ascorbyl palmitate, cetyl palmitate, colfosceril palmitate, ehtylhexyl palmitate, isopropyl palmitate, palmitic acid, palmitoyl-CoA, retinyl palmitate and sucrose monopalmitate.

In one embodiment, a drug ester may be used. The drug ester may be an ester of a drug from one of the following classes: antibiotics, anticonvulsants, antidepressants, antihistamines, anti-parkinsonian drugs, drugs for migraine, headaches, drugs for the treatment of alcoholism, muscle relaxants, anxiolytics, nonsteroidal anti-inflammatories, other analgesics and steroids.

In another embodiment, the ester may be an ester of an acidic drug compound. An ester of an acidic drug compound may be one or more of the following types: C1-C6 straight chain substituted or unsubstituted alkyl ester, C1-C6 branched chain substituted or unsubstituted alkyl ester, C3-C6 substituted or unsubstituted cyclic alkyl ester, C1-C6 substituted or unsubstituted alkenyl ester, C1-C6 substituted or unsubstituted alkynyl ester, and substituted or unsubstituted aromatic ester.

In another embodiment, the ester may be an ester of a drug alcohol. An ester of a drug alcohol may be selected from one or more of the following types: C1-C6 substituted or unsubstituted straight chain alkanoate, C1-C6 substituted or unsubstituted branched chain alkanoate, C1-C6 substituted or unsubstituted alkenoate, and C1-C6 substituted or unsubstituted alkynoate.

In one embodiment, a preferable fatty acid source is the *cannabis* plant itself. Cannabis oil, also known as hemp seed oil, is unique in the plant kingdom as having a fatty acid profile that is readily digestible and contains essential fatty acids required in human nutrition. Additionally, by using *cannabis* oil, the composition of the present invention may be created using a natural approach to the formulation where synthesized and processed components are undesirable. An example fatty acid composition may include, without limitation, 43-62% linoleic acid (LA) omega-6, 19-25% alpha linolenic acid (LNA) omega-3, 7-9% oleic acid omega-9, 2-4.5% gamma linolenic acid, and 1-2% stearidonic acid.

The condensation will now be discussed in greater detail. The condensation may include an aerosol. More specifically, the condensation may include one or more ingredients that can be suspended in a gas. Vaporization and resulting vapors, as they are described through this invention, are intended to include gases, liquids that has been converted into a gas, and a liquid or solid suspended in a gas as an aerosol. Vaporization may occur at approximately 180-190 degrees Celsius, which may significantly reduce pyrolytic smoke compound generation. Additionally, vaporization may occur below the typical point of combustion where smoke and associated toxins are generated, which may be at about 230 degrees Celsius. The condensation may be an aerosol characterized by a mass median aerodynamic diameter (MMAD) of about 0.1 to 5 microns. In another embodiment, the composition may include a condensation aerosol characterized by an MMAD of less than about 3 microns. In another embodiment, the composition may include a condensation aerosol characterized by an MMAD of about 0.2 to about 3 microns. Skilled artisans will appreciate additional with condensation aerosols characterized by other MMADs, including but not limited to, about 0.01, 0.05, 0.1, 0.2, 0.3, 0.4, 0.5, 0.6, 0.7, 0.8, 0.9, 1, 1.1, 1.2, 1.3, 1.4, 1.5, 1.6, 1.8, 2, 2.2, 2.4, 2.6, 2.8, 3, 3.2, 3.5, 4, 4.5, 5, 5.5, 6, 6.5, 7, 8, 9, 10, 11, 12, 13, 14, or 15 microns. Examples of condensation aerosols that may be used with this composition include any colloid of ultra fine particles or liquid droplets such as polyols, e.g., the sugar alcohols. In an exemplary embodiment, the condensation aerosol can be vegetable-derived glycerine.

The carrier will now be discussed in greater detail. The carrier is a substance that promotes mobility and transportation of other substances. The carrier may be an aqueous, semi-aqueous, or other substance. According to an embodiment of the present invention, the carrier may be a liquid solution. Illustrative solutions usable for the carrier include, without limitation, oil in water emulsion, water in oil emulsion, tincture, dispersion suspension, and/or infusion. The carrier may include micro emulsions and/or nano emulsions.

The carrier liquid may include food grade materials. The carrier may also be glycol free and selected to enhance sublingual delivery into the oral mucous membrane, as well as the more conventional oral route, to provide an accelerated onset of the pharmacological effect. The carrier may also be received by the user via inhalation. In one embodiment, the carrier may include ethanol, which may be included for purposes of delivery of the cannabinoid and/or as a recreational alcohol. The ethanol may be derived from wine, sake, grain alcohols, fermented sugars, and/or any other source of consumable alcohol that would be understood by a skilled artisan. Where the carrier is ethanol free, the carrier may include glycerine and/or esters.

Absorption enhancing agents will now be discussed in greater detail. Absorption into mucosa is enhanced by the inclusion of absorption enhancing agents, which may be commonly found in pulmonary drug products, as well as novel compounds such as dimethyl sulfoxide (DMSO), plant lecithins, liposomes, food derived surfactants, fatty alcohols, and other food materials capable of creating a condition of polymorphism. Examples of suitable food-derived surfactants include lecithins, saponins, and those that are carbohydrate-derived. Food-derived surfactants can include ones that are monomeric (e.g., fructose, glucose and sorbitol), polymeric (e.g., cellulose, dextrins, starch, chitin and pectin), or dimeric (e.g., lactose and sucrose). In exemplary embodiments, the food-derived surfactants are one or more sugar-derived surfactants such as, for example, alkyl polyglycosides (APGs), decyl glucoside, and sucrose cocoate. In the most preferred embodiments, the food-derived surfactants are one or more alkyl polyglycosides. Skilled artisans will appreciate polymorphism, as it applies in biophysics, as an aspect of the behavior of lipids that influences their long-range order, i.e. how they aggregate. Examples of polymorphism within the context of the present invention can be in the form of spheres of lipid molecules called micelles. A micelle is an aggregate of surfactant molecules dispersed in a liquid colloid.

Pulmonary gene therapy may require aerosolisation of the gene vectors to the target a region of the lower respiratory tract. Pulmonary absorption enhancing agents may improve penetration of pharmaceutically active or bio-active ingredients in an airway. Compounds acting as absorption enhancing agents may also enhance the aerosolisation properties of sprayed and/or inhaled compounds.

As discussed above, fatty alcohols may be included by the absorption enhancing agent. Examples of fatty alcohols that may be used include, but should not be limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol), elaidolinolenyl alcohol (9E, 12E, 15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), 1-heptacosanol, montanyl alcohol, cluytyl alcohol (1-octacosanol), 1-nonacosanol, myricyl alcohol, melissyl alcohol (1-triacontanol), 1-dotriacontanol, and geddyl alcohol (1-tetratriacontanol).

In an embodiment of the present invention, the absorption enhancing agent may include one or more ingredient to affect the pH of the composition. Normal pH of a buccal space in humans is approximately 7.3 to 7.4. Typically, buccal absorption of aspirin is only 5%. However, lowering the environmental pH by adding a buffer solution may notably increase the absorption rate. As an example, at a pH level of 4.5, the absorption rate may increase 45%-50%. As another example, at pH level of 2.5, the absorption rate may increase to 70%. Virtually any food-use acid may be used for the pH control, including, but not limited to citric, malic, tartric, acetic, benzoic, lactic, butyric, tannic, oxalic, caffeotannic and other food-use acids that would be apparent to a person of skill in the art.

Inclusion of an aromatherapy agent in the composition will now be discussed in greater detail. The composition may include aromatherapy agents. Aromatherapy has been used since ancient times as a natural healing aid, making its inclusion in the composition advantageous to a user. Aromatherapy promotes emotional and physical well-being through the use of essential oils. The aromatherapy agent may be received by the user via vaporization and/or inhalation, as it provides the most direct route to the brain. Essential oils have tiny molecules that, when inhaled, reach the olfactory epithelium. Skilled artisans will appreciate the olfactory epithelium to include two groups of greater than 25 million receptor cells at the top of the nostrils. Here, odors are converted into neurological messages, which may be relayed to the brain for processing.

Historically, users have been exposed to aromatherapy treatments in the form of steams, oils, and vapors. By including the aromatherapy agent in the composition, users can advantageously take advantage of the natural benefits of aromatherapy along with the pharmacological effect induced by the cannabinoid. Therapeutic and recreational aromaceutical benefits may include alleviating sinus congestion, bronchial infection, and the like, enhancing the effect achieved by reception of the composition by a user.

Inclusion of a flavoring agent in the composition will now be discussed in greater detail. The composition may contain flavoring agents to enhance enjoyment of a user while receiving the composition. The composition may also include other therapeutic or recreational agents such as energy enhancing agents and the like. Examples of flavoring agents suitable for use in the composition include those that are oil soluble, e.g., the essential oils, and more preferably, the essential flavor oils, which include mints, spices, and citrus oils. In an exemplary embodiment, the flavoring agent is one or more citrus oils, e.g., citrus oils of orange, tangerine, lemon, lime, or grapefruit.

In an embodiment, the product may contain a tobacco essence, nicotine free tobacco essence, and/or tobacco flavoring to ease the transition away from tobacco products. Inclusion of tobacco-related flavoring may advantageously assist a user with cessation of smoking and nicotine dependence.

In an embodiment of the present invention, the composition may include the above discussed ingredients in varied amounts. In the interest of clarity, illustrative ranges for the ingredients will now be discussed without limitation. Those of skill in the art will appreciate that additional ranges of ingredients may be included in the composition, and should not view the following examples as limiting in any way.

In an illustrative embodiment of the composition, the following ingredients may be included within their respective ranges: *cannabis* at about 0.1-15%, ester and/or fatty acid at about 40-90%, glycerol at about 5%, fatty alcohol at about 5-40%, water at about 0-30%, flavoring at about 0-2%, therapeutic agent at about 0-5%, and organic acid at about 1-5%. In a preferred illustrative embodiment of the composition, the following ingredients may be included within their respective ranges: *cannabis* at about 0.1-9%, ester and/or fatty acid at about 60-85%, glycerol at about 5%, fatty alcohol at about 5-30%, water at about 0-15%, flavoring at about 0-1.5%, therapeutic agent at about 0-3%, and organic acid at about 1-3%. In a more preferred illustrative embodiment of the composition, the following ingredients may be included within their respective ranges: *cannabis* at about 0.1-6%, ester and/or fatty acid at about 70-80%, glycerol at about 5%, fatty alcohol at about 5-20%, water at about 2-10%, flavoring at about 0-1%, therapeutic agent at about 0-1.5%, and organic acid at about 1-2%.

In operation, the composition may be vaporized for delivery to a user. The vaporizer may receive the composition in a liquid form. The vaporizer may then convert the composition into a vapor and/or an aerosol to be inhaled or otherwise received by a user. An example of a vaporizer may include, but should not be limited to, an electronic cigarette.

Those of skill in the art will appreciate the structure and operation of an electronic cigarette. However, in the interest of clarity, an embodiment of a vaporizer as an electronic cigarette will now be discussed briefly. An electronic cigarette vaporizer may include a cartridge, an atomizer, and a battery. The cartridge may include a reservoir to hold a liquid to be vaporized. The atomizer may include a heating element to convert the liquid into a vapor and/or aerosol. Optimally, the atomizer can vaporize the liquid without initiating combustion. The battery may have an electrical charge to power the atomizer and other accessories, for example, an indicator light that illuminates while the electronic cigarette is operating.

Vaporization provides many advantages over traditional combustion based methods of administering cannabinoids. For example, since a vaporizer can convert a composition into a vapor, the levels of each ingredient in the composition, including the cannabinoid, are controllable. Also, since vaporization does not involve combustion, a user may inhale or otherwise receive a bio-active ingredient, for example via inhalation, without being required to receive high levels of tar and various toxins associated with smoking. Vaporization also benefits from advantages such as rapid intake, direct delivery to the bloodstream, enhanced control of over- and under-dosage, and avoidance of respiratory disadvantages associated with combustion-based smoking. As discussed above, vaporization may occur at approximately 180-190 degrees Celsius, which may significantly reduce pyrolytic smoke compound generation. Additionally, vaporization may occur below the typical point of combustion where smoke and associated toxins are generated, which may be at about 230 degrees Celsius.

A method for creating a pharmacological effect using a composition will now be discussed. The method may include vaporizing the composition. As discussed above, the composition may include a bio-active ingredient from a cannabinoid. The method may also include absorbing the compound into a mucosa. Skilled artisans will appreciate mucosa to include linings of mostly endodermal regions. Examples of mucosae that may receive at least part of the compound include buccal mucosa, esophageal mucosa, gastric mucosa, nasal mucosa, olfactory mucosa, oral mucosa, bronchial mucosa, and other mucosae that would be apparent to a person of skill in the art after having the benefit of this disclosure. The method may additionally include receiving the bio-active ingredient of the composition by a cannabinoid receptor and/or an acetylcholine receptor.

Examples of the composition will now be provided without limitation. Skilled artisans will appreciate additional ratios of ingredients after having the benefit of this disclosure, which are intended to be included within the scope and spirit of the present invention.

Example 1

As a Base Example with High Cannabis Content

*Cannabis* resin 6%
Fatty acid 85%
Glycerol 2%
Flavor 2%
Organic acid 1%
Anti oxidant agent 1%

Example 2

For Smoking Cessation

*Cannabis* resin 4%
Fatty acid Q.S.
Glycerol 5%,
Butyl valerate 1%
isopentyl hexonate 1%
Sodium benzoate 0.4%
Ethyl heptylate 0.2%
Hexyl hexanoate 0.3%
Geranyl butyrate 2%

Citric acid 0.5%
Tobacco essence 1.0%

Example 3

Using Aromatherapy Oils

*Cannabis* 2%
Fatty acid 90%
Ciric acid 2.5%
Flavor 1%
Therapeutic oil 4.5%

Example 4

Low *Cannabis* Content

*Cannabis* 0.1%
Fatty acid 80%
Glycerol 5%
Fatty alcohol 8%
Water 2.9%
Flavor 1%
Therapeutic agent 1%
Organic acid 2%

Without limitation, an illustrative analysis and comparison of a vapor produced using an embodiment of the present invention and smoke produced with traditional administration methods will now be discussed. The study consisted of two phases. First, a quantitative analysis of the solid phase of the vapor using high performance liquid chromatograph (HPLC) to determine the amount of cannabinoids delivered. Second, a gas chromatograph/mass spectrometry (GC/MS) analysis of the gas phase was performed to analyze the vapor for a wide range of toxins, focusing on pyrene and other polynuclear aromatic hydrocarbons (PHAs). Vapor was generated by loading a commercially available electronic cigarette with 200 mg samples of *cannabis* solution. For comparison purposes, a second 200 mg sample was combusted in an enclosed vessel.

In the first step of the study, a vapor according to the embodiments of the present invention was analyzed using the HPLC. Analysis of the vapor found that the semi-aqueous solution as described above delivered 37%-65% of the THC in the test sample. This concentration of THC is comparable to the same THC levels found in smoke inhaled from a marijuana cigarette.

Additionally, in the second step of the study, the gas chromatograph and mass spectrophotometer analysis showed that the gas phase of the vapor was consists of a majority of cannabinoids, with trace amounts of three to five other compounds. This marked a significant improvement over combustion-based delivery of cannabinoid substances, which typically include well over 100 ancillary compounds identified in combusted marijuana smoke from a conventional marijuana cigarette. The results indicate that the vaporization of the solution of the present invention can deliver therapeutic doses of cannabinoids with a drastic reduction in pyrolytic smoke compounds.

The conclusion of this test was the dramatic reduction in non-cannabinoid compounds in the vapor from the aqueous solution, demonstrating that the novel vaporization composition and method of the present invention provides an effective technique for delivering active cannabinoids while suppressing other potentially dangerous and harmful compounds that are a byproduct of normal cigarette combustion processes.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for creating a pharmacological effect to treat diseases, conditions, and symptoms of illness that are treatable using a composition comprising a cannabinoid, the method comprising the steps of:
   (a) vaporizing the composition, wherein the composition comprises:
   a bio-active ingredient comprising a cannabinoid that is capable of inducing the pharmacological effect, wherein the cannabinoid is selected from the group consisting of dodeca-2E,4E,8Z,10E/Z-tetraenoic-acid-isobutylamides, cannabichromene, cannabicyclol, cannabivarin, tetrahydrocannabivarin, cannabidivarin, cannabichromevarin, cannabigerovarin, and cannabigerol monomethyl ether, an ester, a condensation aerosol, and a carrier liquid solution of food grade materials;
   (b) absorbing the composition into a mucosa; and
   (c) receiving the bio-active ingredient of the composition by a cannabinoid receptor or an acetylcholine receptor.

2. The method of claim 1, wherein the mucosa comprises an oral mucous membrane, and wherein the carrier liquid solution enhances sublingual delivery into the oral mucous membrane to provide accelerated onset of the pharmacological effect.

3. The method of claim 1, wherein the cannabinoid is derived from at least one cannabinoid source selected from the group consisting of *Cannabis sativa, Cannabis indica, Cannabis ruderalis, Echinacea purpurea, Echinacea angustifolia, Echinacea pallida, Acmella oleraca, Helichrysum umbraculigerum*, and *Radula marginata*.

4. The method of claim 3, wherein the ester is derived from the cannabinoid source comprises ascorbyl palmitate, sucrose monopalmitate, or a combination of the foregoing.

5. The method of claim 1, wherein the bio-active ingredient comprises dodeca-2E,4E,8Z,10E/Z-tetraenoic-acid-isobutylamides.

6. The method of claim 1, wherein the composition further comprises ethanol.

7. The method of claim 1, wherein the composition further comprises an absorption enhancing agent that creates a condition of polymorphism to enhance absorption into the mucosa.

8. The method of claim 7, wherein the absorption enhancing agent further comprises at least one ingredient selected from the group consisting of dimethyl sulfoxide, plant lecithins, liposomes, food derived surfactants, and fatty alcohols.

9. The method of claim 1, wherein the composition further comprises a flavoring agent.

10. The method of claim 1, wherein the bio-active ingredient further comprises cannabidiol.

11. The method of claim 1, wherein the bio-active ingredient further comprises cannabinol.

12. The method of claim 1, wherein the bio-active ingredient further comprises cannabigerol.

13. The method of claim 1, wherein the bio-active ingredient further comprises tetrahydrocannabinol.

14. The method of claim 13, wherein the bio-active ingredient further comprises at least one additional cannabinoid selected from the group consisting of tetrahydrocannabinol, cannabidiol, cannabinol, cannabigerol, cannabichromene, cannabicyclol, cannabivarin, tetrahydrocannabivarin, cannabidivarin, cannabichromevarin, cannabigerovarin, and cannabigerol monomethyl ether.

15. A method for creating a pharmacological effect to treat diseases, conditions, and symptoms of illness that are treatable using a composition comprising a cannabinoid, the method comprising the steps of:
   (a) vaporizing the composition, wherein the composition comprises:
   a bio-active ingredient comprising a cannabinoid that is capable of inducing the pharmacological effect, wherein the cannabinoid comprises dodeca-2E,4E,8Z,10E/Z-tetraenoic-acid-isobutylamides, an ester, a condensation aerosol, and a carrier liquid solution of food grade materials;
   (b) absorbing the composition into a mucosa; and
   (c) receiving the bio-active ingredient of the composition by a cannabinoid receptor or an acetylcholine receptor.

16. The method of claim 15, wherein the bio-active ingredient further comprises a cannabinoid selected from the group consisting of tetrahydrocannabinol, cannabidiol, cannabinol, cannabigerol, cannabichromene, cannabicyclol, cannabivarin, tetrahydrocannabivarin, cannabidivarin, cannabichromevarin, cannabigerovarin, and cannabigerol monomethyl ether.

* * * * *